US005489288A

United States Patent [19]

Buelna

[11] Patent Number: 5,489,288
[45] Date of Patent: * Feb. 6, 1996

[54] DEVICE AND METHOD FOR APPLYING LARGE-DIAMETER LIGATING LOOP

[75] Inventor: Terry Buelna, Long Beach, Calif.

[73] Assignee: Advanced Surgical, Inc., Princeton, N.J.

[ * ] Notice: The portion of the term of this patent subsequent to Apr. 5, 2011, has been disclaimed.

[21] Appl. No.: 223,261

[22] Filed: Apr. 4, 1994

Related U.S. Application Data

[63] Continuation-in-part of Ser. No. 758,909, Oct. 9, 1992, Pat. No. 5,300,078.

[51] Int. Cl.$^6$ .................................................. A61B 17/12
[52] U.S. Cl. ........................ 606/144; 242/388.6; 242/389
[58] Field of Search .................................. 606/113, 139, 606/144, 145, 146, 148, 228, 108

[56] References Cited

U.S. PATENT DOCUMENTS

| | | |
|---|---|---|
| 659,422 | 10/1900 | Shidler . |
| 2,610,631 | 9/1952 | Calicchio . |
| 3,476,115 | 11/1969 | Graeff et al. . |
| 3,665,926 | 5/1972 | Flores . |
| 3,985,138 | 10/1976 | Jarvik . |
| 4,592,355 | 6/1986 | Antebi . |
| 5,007,914 | 4/1991 | Schweigerling ............... 606/108 |
| 5,084,054 | 1/1992 | Bencini et al. ................ 606/113 |
| 5,129,912 | 7/1992 | Noda et al. .................... 606/139 |
| 5,300,078 | 4/1994 | Buelna ........................... 606/113 |
| 5,334,199 | 8/1994 | Yoon .............................. 606/144 |

FOREIGN PATENT DOCUMENTS

| | | |
|---|---|---|
| 552077 | 3/1977 | U.S.S.R. . |
| 835429 | 6/1981 | U.S.S.R. . |
| 1169630 | 7/1985 | U.S.S.R. . |
| 868634 | 5/1961 | United Kingdom . |

*Primary Examiner*—Tamara L. Graysay
*Attorney, Agent, or Firm*—Burns, Doane, Swecker & Mathis

[57] ABSTRACT

A suture applying device comprises an elongate shaft having a length of suture therein. A pre-tied loop suture is held at the distal end of the shaft with a free end of the suture being attached within a handle secured to the proximal end of the shaft. In a first embodiment, a pulley and puller assembly is provided for closing the pre-tied suture loop, where the pulley permits a greater length of suture to be taken in than is traveled by the puller. In a second embodiment, a pair of opposed jaws are slidably mounted within the handle for selectively engaging and gripping the free end of the suture. In this way, an arbitrarily large length of suture may be taken in by pulling on the free end of the suture in successive strokes. The device further includes a sheath slidably disposed on the shaft for protecting the suture during introduction. The sheath automatically retracts when the device is introduced through a trocar sleeve or cannula, thereby exposing the suture loop.

38 Claims, 14 Drawing Sheets

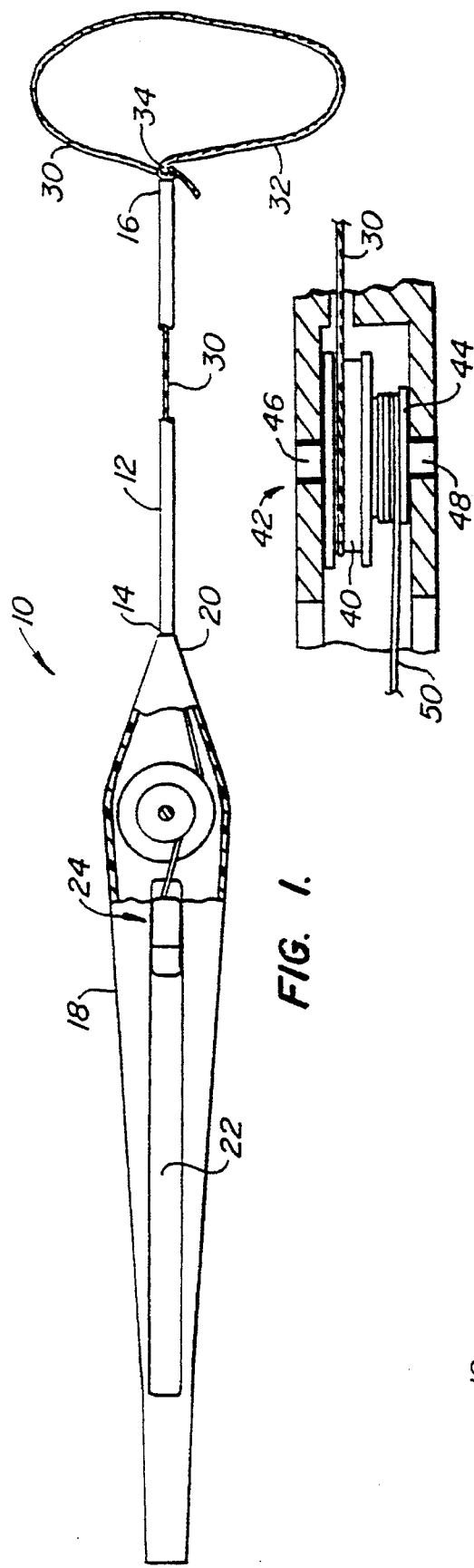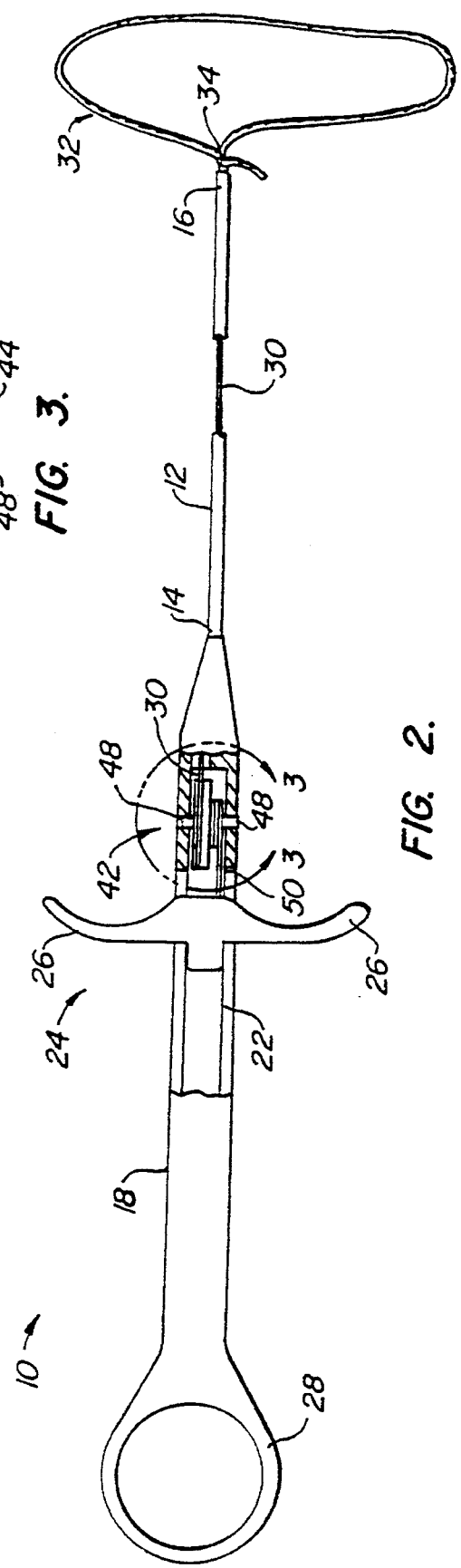

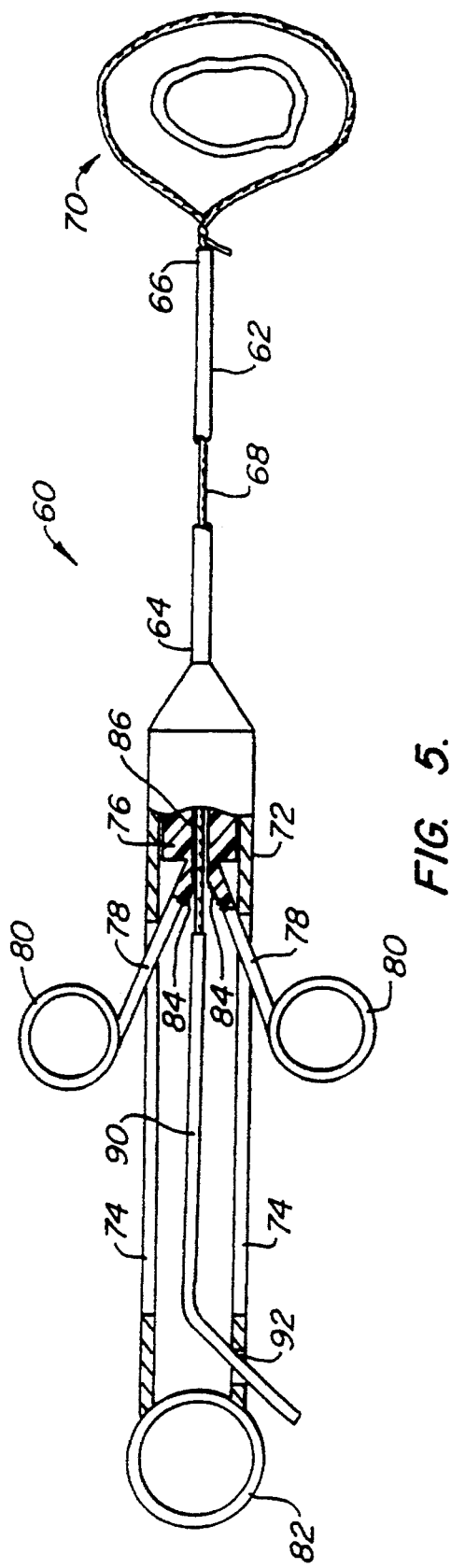
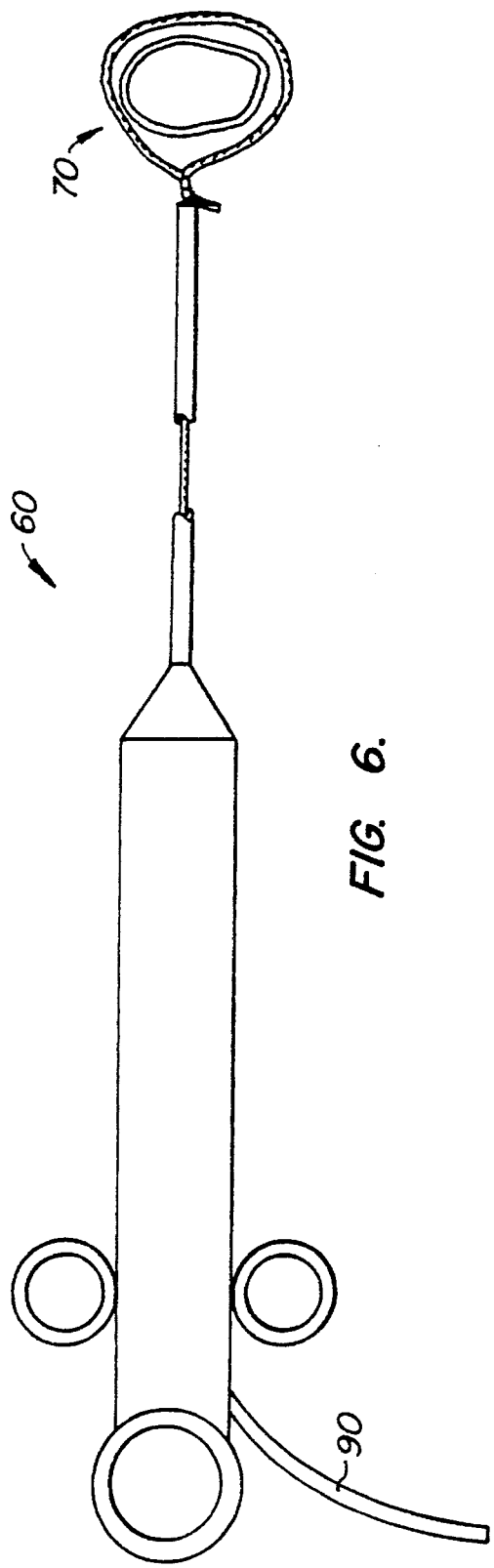
FIG. 5.
FIG. 6.

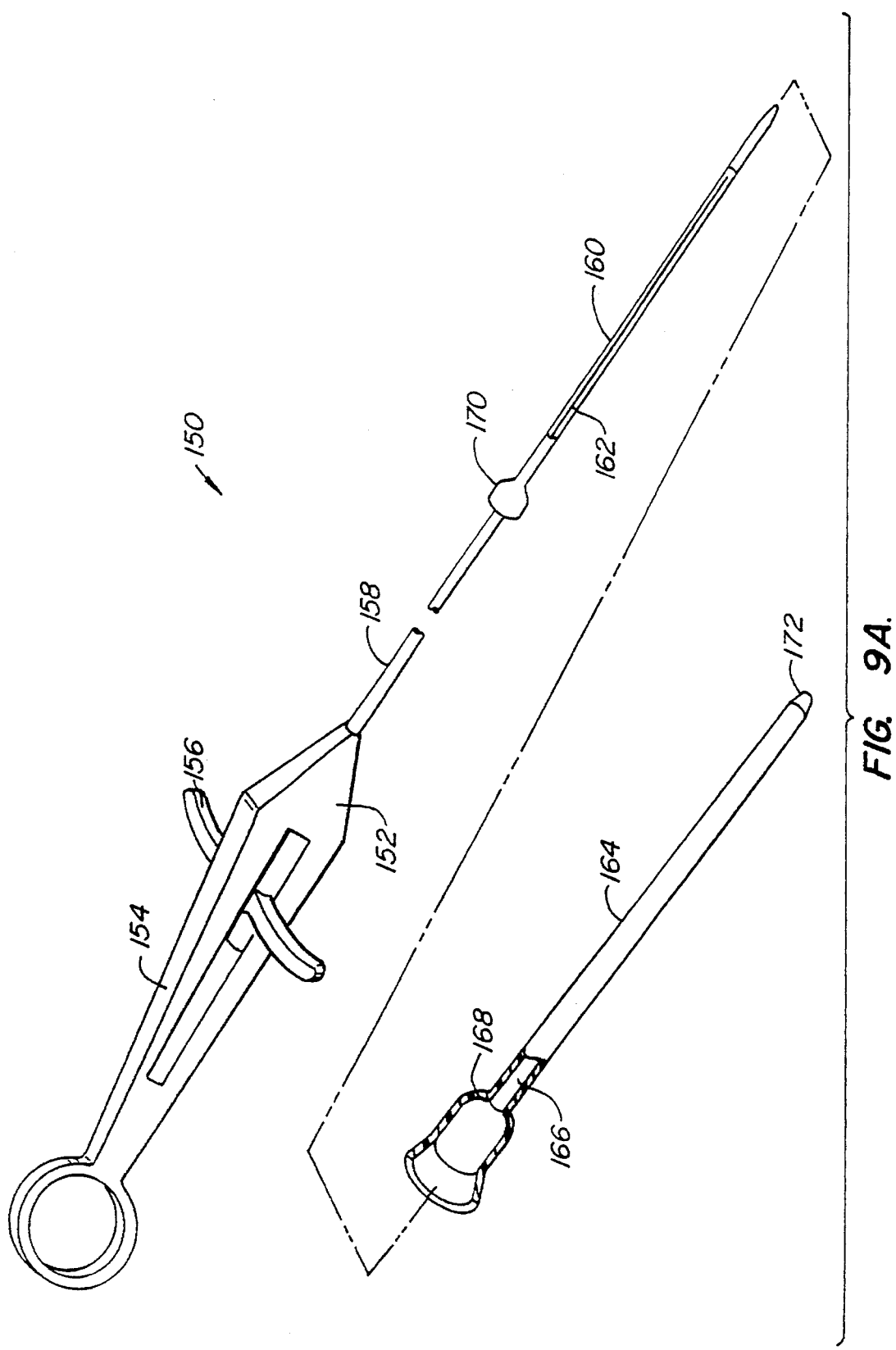

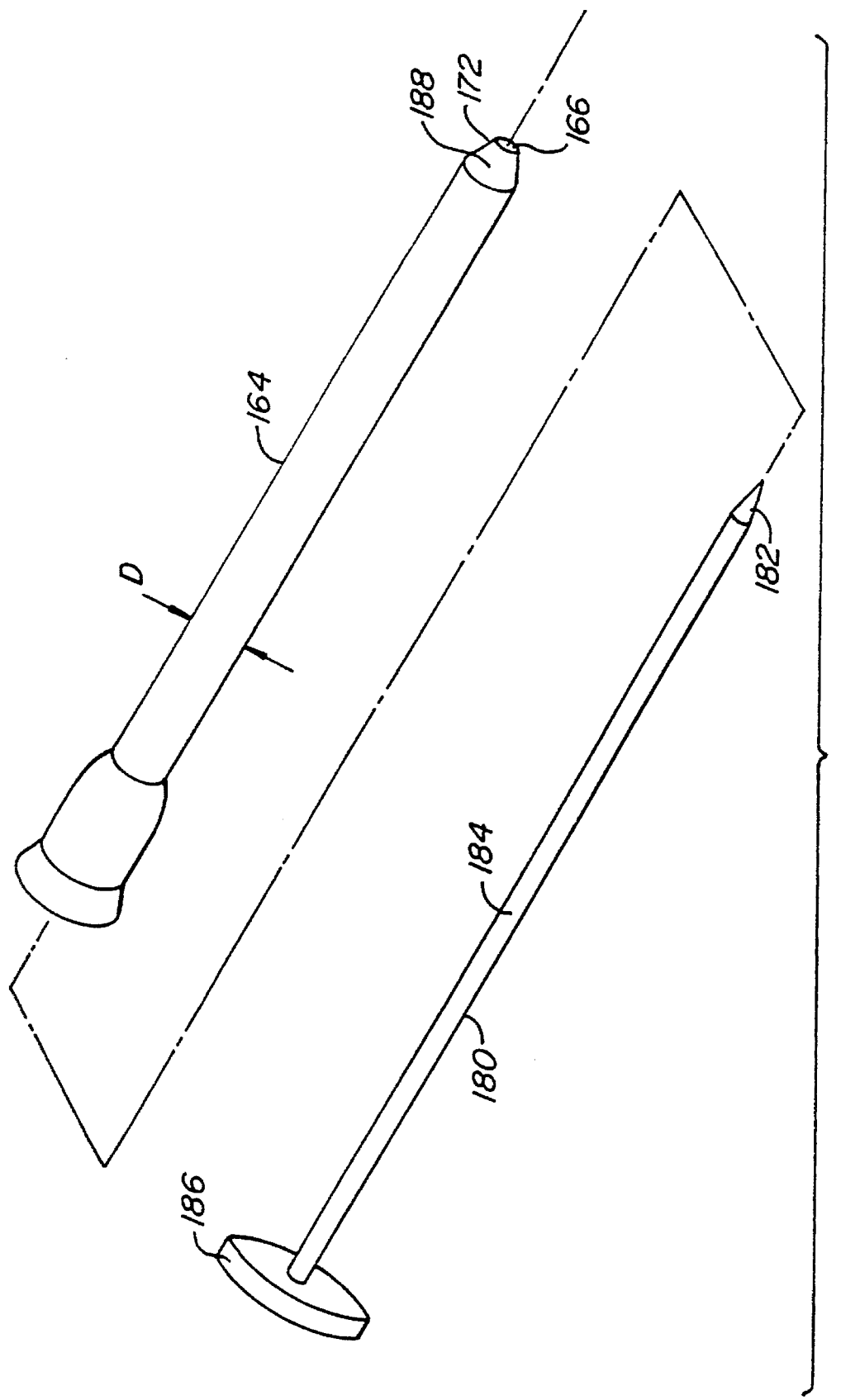

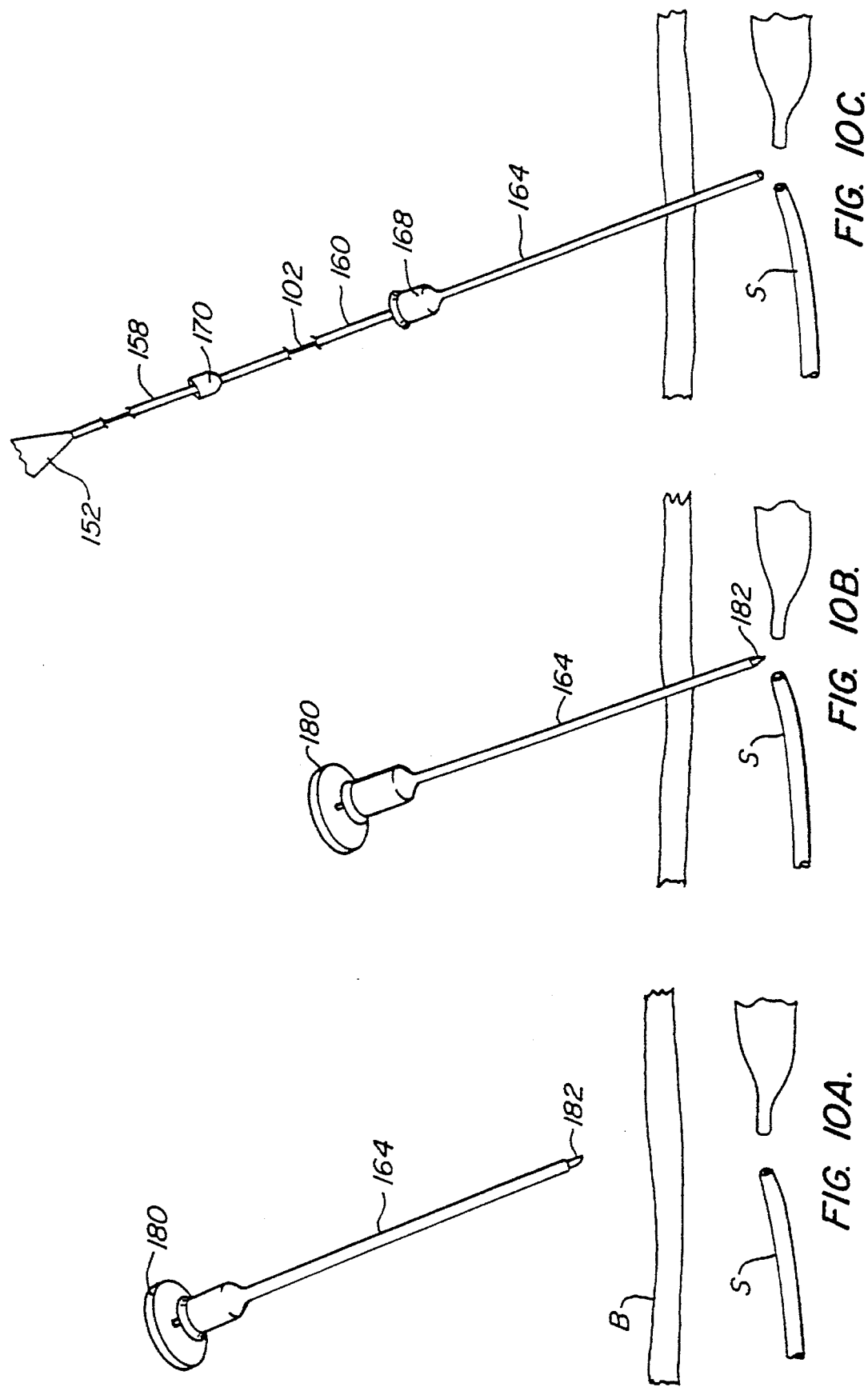

5,489,288

DEVICE AND METHOD FOR APPLYING LARGE-DIAMETER LIGATING LOOP

CROSS REFERENCE TO RELATED APPLICATIONS

This application is a continuation in part application of patent application Ser. No. 07/958,909 filed Dec. 9, 1992, now U.S. Pat. No. 5,300,078.

BACKGROUND OF THE INVENTION

1. Field of the Invention

The present invention relates generally to devices and methods for ligating body structures and, more particularly, to devices for positioning a preformed ligating loop around the body structure and tightening the loop using a device which can be manipulated with a single hand.

Pre-tied ligating loops are utilized in surgical procedures for a variety of purposes. Most commonly, the ligating loops will be placed around the outside of a severed body lumen, such as a blood vessel or the cystic duct, tightened by pulling on a free end of the ligature, and severed using separate severing shears. Usually, the ligating loop will be mounted on the end of a rod or tube so that the surgeon may hold the knot in place with the tube while pulling on the free end of the ligature to tighten the loop.

One form of a ligating loop applier comprises a hollow tube carrying the ligating loop at its distal end. The free end of the suture is threaded proximally through the lumen of the tube and secured to the proximal end of the tube. A small section of the tube near the proximal end is weakened so that it may be easily broken off by the surgeon. By breaking the proximal end off, and pulling proximally on the suture, the ligating loop at the distal end of the tube may be tightened.

While such ligating loop appliers are commonly employed in surgery, including laparoscopic surgery, they suffer from requiring two hands for use, i.e. a first hand to hold the suture applying tube and a second hand to break off and pull on the proximal end of the tube. Manipulation is further complicated by the need to use a stainless steel tube to protect the loop as it is being introduced through a conventional trocar sleeve of the type used in laparoscopic surgery. Additionally, use of such loop appliers has generally been limited to insertion through conventional 5 mm trocar sleeves which have been pre-positioned at particular locations in the body. The number and size of such trocars should be minimized in order to minimize trauma. It would often be desirable to insert the loop appliers through other locations without the need to position additional trocar sleeves or to withdraw other instruments which are already in place in the existing trocar sleeves.

It would therefore be desirable to provide improved suture applying devices which can be manipulated using a single hand, including both placement of the loop about a target body structure and tightening of the loop using only the single hand. Most desirably, the device could be introduced through a cannula of reduced diameter to minimize trauma.

A useful design for such a "single-handed" ligating loop applier would employ a three-finger actuating assembly, including an actuator which is engaged by the users middle and index fingers and a thumb rest at the proximal end of the device. By attaching the free end of the suture to the actuator, the user could first position a ligating loop held at the distal end of the device at a desired target location and thereafter tighten the loop by translating on the actuator by closing the middle and index finger in opposition to the thumb. Such a design, however, suffers from the drawback that the loop-closing stroke is limited in length so that pre-tied loops of only about 2–3 cm in diameter can be closed.

To overcome such a limitation on loop size, it has been proposed that a post be placed on the puller of the ligature applying device and that the free end of the suture be wrapped about the post with the end tied to a portion of the device which remains stationary relative to the puller. When the puller is drawn proximally, a length of suture equal to twice the length of translation will be drawn in. In this way, larger ligating loops can be closed in a single stroke. An exemplary ligating design of this type is described in U.S. Pat. No. 2,610,631.

While workable and an improvement in many ways over other suture-applying devices, ligators of the type described in the '631 patent suffer from certain disadvantages. First, the ratio of suture uptake to puller travel is limited to a factor of 2. While it would be theoretically possible to wrap the suture around a second post on the ligator body and attach the free end of the puller (thus increasing the ratio to a factor of 3), such additional turns of the suture would increase the chances that the suture would become tangled while the loop applier is in use. Additional turns further compromise the device by increasing the friction between the suture and the posts, thereby reducing the ease of actuation. Moreover, the utility of the device is limited in laparoscopic and endoscopic or other cannula procedures where the applier must be introduced through a trocar sleeve, since the presence of the suture on the exterior of the ligator increases the changes that the suture will become tangled during introduction. Additionally, presence of the coupling mechanism between the puller and the suture on the exterior of the device increases the opportunity for contamination and jamming.

For these reasons, it would be desirable to provide improved devices and methods for applying pre-tied ligating loops to body structures, where the devices and methods are suitable for applying large-diameter ligating loops using a single device in a single hand. Such devices should be of relatively simple construction and should be relatively simple to use. In particular, it would be desirable if the suture be contained completely or almost completely within the interior of the device and that the design reduce the opportunity for the suture to become entangled during use. It would be further desirable to provide systems which permit insertion of the suture through conventional trocar sleeves or other cannulas, where the suture is protected by a sheath which is automatically retracted as the suture is passed through the cannula.

2. Description of the Background Art

U.S. Pat. No. 2,610,631, is described above. U.S. Pat. No. 3,476,115, describes a ligating loop applier comprising a single tube having a frangible proximal end, where the proximal end is attached to a free end of the suture and may be broken off so that a suture loop at the distal end may be drawn closed. U.S. Pat. No. 5,129,912, describes a suture applying device, where a pre-tied suture loop is used for laparoscopic and endoscopic knot tying. Other devices are described in U.S. Pat. Nos. 4,592,355; 3,985,138; 3,665, 926; 659,442; U.S.S.R. Patent Publications 1,169,630; 835, 429; 552,077; and U.K. Patent 868,634.

SUMMARY OF THE INVENTION

According to the present invention, a suture applying and tightening device comprises a hollow shaft which carries a length of suture therethrough having a first free end and a second end which is formed into a loop. In particular, the loop will be pre-tied with a slip knot which permits the loop to be tightened by pulling on the free end of the suture while the knot is held in place. The knot in the pre-tied suture loop will be held on the distal end of the shaft so that pulling back on the free end of the suture through the sheath will tighten or close the loop about a body structure. Typically, the shaft will be a tube having an axial lumen, and the free end of the suture will pass proximally through the lumen while the pre-tied knot is held on a distal port of the lumen.

In a first embodiment of the apparatus of the present invention, a handle assembly is attached to the proximal end of the shaft, and the handle assembly includes a slidably mounted puller and a pulley having a small-diameter wheel and a large-diameter wheel. The small-diameter wheel and large-diameter wheel will usually be mounted coaxially, and will more usually be formed integrally, so that they will rotate in unison. The free end of the suture will be attached to the large-diameter wheel, while a connector line will be secured between the small-diameter wheel and the puller. In particular, the puller will be mounted proximally of the pulley so that drawing proximally on the puller will cause a length of the suture to be drawn proximally along or through the shaft. The length of the suture taken in by the pulley will be some multiple or factor greater than the length of travel of the puller, depending on the ratio between the small diameter and large diameter. Usually, large diameter will be at least twice the small diameter, resulting in a factor of 2 between the length of suture taken in and the length of puller travel. The ratio, however, may be greater than 2, often being 3, 4, or more.

It will appreciated that alternate actuator mechanisms may be provided within the interior of the handle assembly. For example, the actuator may include a pulley assembly, generally as described above, where the small-diameter wheel is a gear wheel. The pulley may then be actuated by a pusher rod having a gear face which mates with the small wheel. In this way, pushing on the rod can cause rotation of the pulley, having the same mechanical advantages described above for the puller assembly. The actuator mechanism could also provide for a pulley mounted on the puller. The free end of the suture could then be passed over the pulley and attached to the interior of the handle assembly. Proximal actuation of the puller would then provide for the desired mechanical advantage in pulling back the suture. A variety of other equivalent mechanical structures could also be provided.

A method according to the present invention utilizing the first embodiment of the apparatus thus comprises positioning a pre-formed loop of suture over the target body structure and thereafter translating the actuator relative to the shaft. The apparatus will be manipulated by the physician using a single hand, typically with the index and middle fingers on the puller and thumb on the proximal end at the apparatus, typically on a thumb rest. A single stroke of the actuator will be all that is required for closing even a relatively large-diameter suture loop, having a diameter of 5 cm or larger.

A second embodiment of the apparatus of the present invention comprises a shaft which carries a pre-tied suture loop in a manner similar to that described for the first embodiment. The second embodiment will also include a handle assembly attached to the proximal end of the shaft, wherein the handle assembly includes a mechanism for selectively engaging and translating the free end of the suture, whereby the free end may be successively drawn proximally to close the loop, typically in two or more strokes. The suture engaging and translating mechanism preferably comprises a pair of opposed jaws, where each jaw includes an attached finger retainer and wherein the handle includes a thumb retainer. Thus, the treating physician may manipulate the device by placing the index and middle fingers in or on the finger retainers and thumb against the thumb retainer, so that the jaws may be closed and drawn proximally using the fingers in opposition to the thumb. Usually, the jaws will be spring-biased so that they remain open in the absence of closing pressure from the physicians fingers. The jaws will also usually include gripping surfaces which help secure the suture when the jaws are closed on one another and drawn proximally.

The apparatus according to the second embodiment will further include means for holding the free end of the suture under tension between each stroke of the jaws. Usually, the holding means will comprise a support tube attached to the proximal end of the suture, the support tube extending through and frictionally engaging as aperture in the handle. Between each stroke of the jaws, the support tube maintains tension in the suture until the jaws reengage the free end.

In a method according to the present invention utilizing the second embodiment of the apparatus, the pre-formed suture loop is first positioned over the body structure and the jaws thereafter engaged against the free end of the suture which passes therebetween. The treating physician may then draw proximally on the jaws using the finger retainers in opposition to the thumb. The process will usually be repeated one or more times in order to draw a sufficient length of suture to completely close the pre-tied loop. It will be appreciated that the device can close the loop of virtually any diameter using only a single hand by repeating successive strokes using the jaws.

Any of the loop applying apparatus of the present invention may be utilized in a system for applying and tightening a suture loop comprising a suture loop applier having a sheath slidably mounted on a distal end of the shaft. The sheath covers and protects the suture loop which extends from the distal end of the shaft, but may be proximally translated to expose the suture loop after it has been introduced through a narrow diameter trocar sleeve or other cannula to a target site. Typically, the sheath will include a protrusion near its proximal end configured to engage a point near the proximal end of the cannula. The cannula may include a restriction near its proximal end which will interfere with the protrusion. Introduction of the sheath through the trocar sleeve will thus result in an interference between the protrusion and the cannula, which prevents the sheath from passing entirely through the cannula, and causes the sheath to retract over the shaft of the suture loop applier. Thus, the suture loop will be automatically exposed through the distal end of the cannula as the suture applier is inserted therethrough using a single hand. In a preferred aspect, the cannula will be combined with a stylet so that it may be self-introduced. Thus, the suture applier can be positioned at any insertional location without the need for a pre-positioned incision or trocar. The cannula and stylet may be of substantially smaller diameter than conventional trocars, minimizing trauma in the patent.

Alternative embodiments of the suture applying system include a cannula having a restriction at the proximal end, the distal end, or a point midway between the two ends. These restrictions engage the distal end of the sheath which is configured to be larger than the restriction thus causing the sheath to be retracted and allowing the suture to be uncovered. These embodiments thus prevent the sheath from travelling through the distal end of the cannula and into a patient's body cavity.

Other alternative embodiments of the suture applying system include a sheath having a score along an axial line thereby allowing the sheath to split as the handle is advanced through the sheath. With this configuration, longer sheath lengths which accommodate larger loop sizes can be used. Alternatively, the sheath is configured to be axially compressible. This may be accomplished by constructing the sheath of a braided or woven mesh material, or by a tube having a convoluted wall.

BRIEF DESCRIPTION OF THE DRAWINGS

FIG. 1 is a side elevational view of a first embodiment of the suture applying device of the present invention.

FIG. 2 is a top plan view of the suture applying device of FIG. 1, with portions broken away.

FIG. 3 is a detailed view of the pulley system of the suture applier of FIGS. 1 and 2, taken along line 3—3 of FIG. 2.

FIG. 5 is a top plan view of a second embodiment of the suture applier of the present invention, shown with portions broken away.

FIG. 6 is a top plan view, similar to FIG. 5, except that the free end of the suture has been retracted and the suture loop has been partially closed.

FIG. 9A is a perspective view of a suture applying system constructed in accordance with the principles of the present invention.

FIG. 9B is a perspective view of the stylet and cannula of the suture applying system of FIG. 9A.

FIGS. 10A–10F illustrate use of the system of FIG. 9 in applying suture to a severed body duct according to the method of the present invention.

DESCRIPTION OF SPECIFIC EMBODIMENTS

The suture applying device of the present invention comprises an elongate shaft which carries a suture loop at its distal end. The suture loop includes a pre-tied slip knot and a free end extending from the slip knot so that pulling on the free end in a proximal direction will tighten the loop over a target body structure. The present invention further comprises a mechanism on the device for pulling on the free end of the suture in a proximal direction, where the mechanism enables the treating physician to proximally draw sufficient length of suture to close even relatively large suture loops. In a first embodiment, the mechanism comprises a pulley assembly, as described in more detail hereinafter. In a second embodiment, the mechanism comprises a pair of spring-biased opposed jaws, as described in more detail hereinafter.

The shaft of the suture applying device will be an elongate structure, typically being a tube or cylinder having a diameter small enough to be used in laparoscopic, endoscopic, and similar procedures. Typically, the shaft will have a width or diameter in the range from about 1.5 mm to 2 mm. The length of the shaft will be sufficient to permit use of the device in such laparoscopic, endoscopic, and similar procedures, typically being from about 20 cm to 30 cm, usually being from 23 cm to 25 cm. It will be appreciated that the shaft diameter need not be uniform over its entire length and that the narrow diameter portion need only be long enough to permit access through a narrow incision, trocar sleeve or other cannula being used in the procedure. The shaft may be composed of a variety of materials, usually being surgical stainless steel, polycarbonate resin, or the like. A handle assembly will be attached to the proximal end of the shaft and will be used by the treating physician to manipulate the device during use. The handle will typically comprise an elongate body having a hollow interior and defining a track for a puller or jaw mechanism for retracting the free end of the suture, as described in more detail hereinafter. The handle may also be formed from a variety of materials, such as surgical stainless steel, polycarbonate resin, and the like. The puller or jaw mechanism will usually include a pair of finger retainers, i.e. "ears", or rings, disposed on or within the track, and an opposed thumb retainer or ring disposed on the proximal end of the handle. In this way, the user can hold the handle between the middle and index fingers while applying proximal force on the finger retainers.

Figure 4:
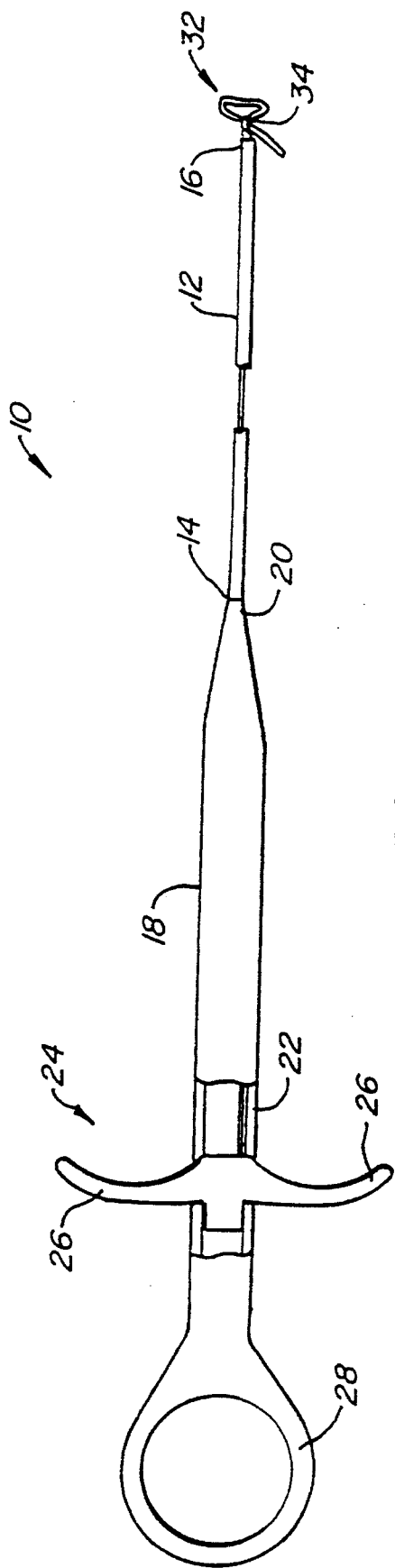
FIG. 4 is a top plan view of the suture applier of FIGS. 1 and 2, shown with the suture loop in a closed configuration.

Referring now to FIGS. 1–4, a first specific embodiment 10 of the suture applying device of the present invention will be described. The suture applying device 10 comprises a shaft 12 having a proximal end 14 and a distal end 16. An elongate handle 18 is secured at its distal end 20 to the proximal end 14 of shaft 12. Handle 18 includes a hollow interior and defines an elongate slot 22. A puller 24 including a pair of finger-retaining ears 26 is slidably mounted in the slot 22 so that it may be shifted between a distal position (FIGS. 1 and 2) and a proximal position (FIG. 4). The handle 18 will typically terminate in a thumb retainer, such as thumb ring 28 at its proximal end. In this way, the treating physician may hold the device 10 with the thumb within thumb retaining ring 28 and middle and index fingers on the finger retaining ears 26, in a conventional manner.

A length of suture 30 includes an open loop 32 and a free end extending proximally from the open loop. The open loop 32 is held outside the distal tip 16 of shaft 12 with a slip knot 34 being located adjacent an open distal port of the lumen in the shaft. The free end of suture 30 passes through the open port and proximally through the lumen of the shaft 12. After passing through the lumen, the free end of suture 30 enters the interior of housing 18 where it is received on a large-diameter wheel 40 of a pulley assembly 42, best illustrated in FIG. 3. The pulley assembly 42 also includes a small-diameter wheel 44, and the large-diameter wheel 40 and small-diameter wheel are mounted coaxially on a shaft 46 held in a pair of opposed bearings 48 in the housing.

A connector line 50 is secured between the small-diameter wheel 44 and the puller 24. When the puller is in its proximal-most position, as illustrated in FIGS. 1 and 2, the connector line 50 will be wrapped around the small-diameter wheel 44 a number of times, typically at least about 5 times. The free end of suture 30, in contrast, will be attached to the large wheel 40, but will not necessarily be wrapped around the wheel at all. In this way, as the puller 24 is axially translated along slot 22 in a proximal direction, the connector line 50 will unwind and cause the pulley assembly 42 to rotate. Such rotation, in turn, will cause the large-diameter wheel 40 to take-in the free end of suture 30. In particular, the length of suture 30 being taken in for each turn of the pulley will be greater than the length of connector line 50 which is drawn out. The ratio between the suture and length of connector line 50 will be equal to the ratio between the large-diameter and small-diameter. That is, when the large-diameter is twice the small-diameter, for each unit length of connector line 50 which is drawn proximally by puller 24, two unit lengths of the free end of suture 30 will be drawn in on large-diameter wheel 40. This ratio can, of course, be increased by increasing the size of large-diameter wheel 40 relative to small-diameter wheel 44 or decreasing the size of the small-diameter wheel relative to the large-diameter wheel.

As illustrated in FIG. 4, when the puller 24 has been drawn fully proximally within the slot 22, the loop 32 will be essentially completely closed. The initial size of loop 32 may be arbitrarily large, with the ratio between the large-diameter and small-diameter being selected to provide sufficient uptake length to close the loop. Usually, the loop 32 will be at least 5 cm in diameter, but may be as large as 7.5 cm in diameter, or even as large as 10 cm in diameter. The ratio between the large diameter and small diameter will usually be at least about 2, frequently being at least about 3, and sometimes being 4 or greater.

Figure 1A:
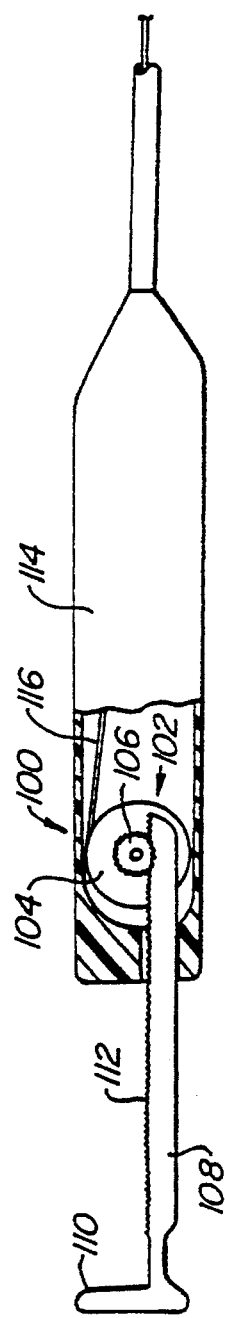
FIG. 1A illustrates an alternative actuation mechanism for the first embodiment of the suture applying device of the present invention.

Referring now to FIG. 1A, an alternate actuation mechanism for the embodiment of FIGS. 1–4 is illustrated. The actuation mechanism 100 comprises pulley 102 including a large-diameter take-up wheel 104 and a small-diameter gear wheel 106. An actuation rod 108 having a thumb rest 110 and a gear face 112 is mounted within the device handle 114 so that it may be translated axially by pressing on the thumb rest. The gear face 112 mates with the small-diameter gear wheel 106 so that proximal axial movement of the rod 108 will cause counter-clockwise rotation of the pulley 102. Such rotation will take up a free end of suture 116, thus closing a suture loop (not illustrated) in a manner similar to that described above.

Referring now to FIGS. 5 and 6, a second embodiment 60 of the device of the present invention will be described. The device 60 includes a shaft 62 having a proximal end 64 and a distal end 66. A length of suture 68 is held within the shaft 62, generally as described for suture 30 in FIGS. 1–4, and includes a pre-tied loop 70 at its distal end.

A handle 72 is secured to the proximal end 64 of shaft 62 and includes a hollow interior with a pair of slots 74 formed along its length. A suture engaging mechanism 76 is disposed within the interior of handle 72 and comprises a pair of opposed jaws 78 which extend laterally outward through the slots 72. Each jaw 78 terminates in a finger retainer 80, typically in the form of a finger ring, and the proximal end of the handle 72 terminates in a thumb retainer typically also a ring 82.

The jaws 78 include opposed gripping surfaces 84 which are disposed near a fulcrum point where the jaws converge. Suture 68 extends through an axial passage 86 formed through the engaging element 76. The suture also passes between gripping surfaces 84 of the jaws 78, so that the user may clamp the gripping surfaces down on the suture by pressing inwardly on the finger rings 80. Usually, this will be accomplished as the user holds the device using the thumb, middle finger, and index finger, in a conventional manner. The user may simply tighten on the finger retaining rings 80 using the middle and index fingers and thereafter draw the engaging member 76 proximally backward, to the configuration shown in FIG. 6. A single proximal stroke, as just described, will usually be insufficient to close a relatively large pre-tied loop 70. Should the loop 70 need to be further tightened, the user may loosen the grip on finger retaining rings 80 so that the gripping surfaces 84 disengage the suture 68. The engaging element 76 may then be axially advanced in the distal direction, the jaws again tightened using the finger rings 80, the suture again drawn proximally to further tighten loop 70. Such tightening strokes can be repeated as many times as necessary to fully close the loop 70.

In a preferred aspect of the suture applying device 60, a support tube 90 is attached to the proximal end of suture 68 and passes through an aperture 92 formed in the handle 72. The support tube will frictionally engage an aperture 92 so that the free end of suture 68 is held in place when the jaws 78 are disengaged from the suture. This is particularly helpful while the suture loop 70 is being incrementally closed using the jaws 78 since it will inhibit or prevent slackening of the suture within the device.

Figure 7:
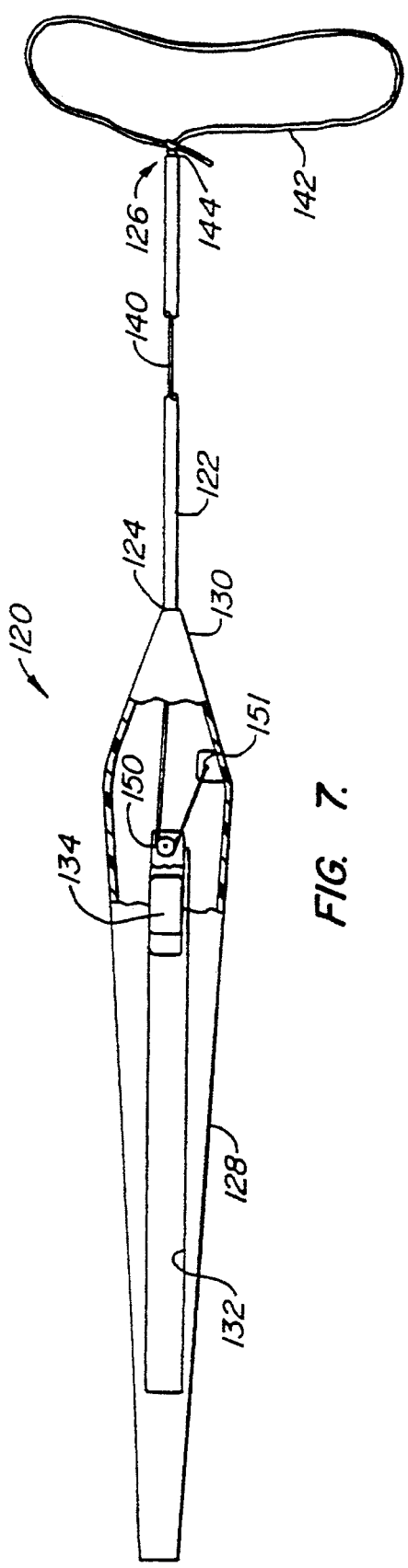
FIG. 7 is a side elevational view with portions broken away of an alternative embodiment of a suture applying device constructed in accordance with the principles of the present invention.
Figure 8:
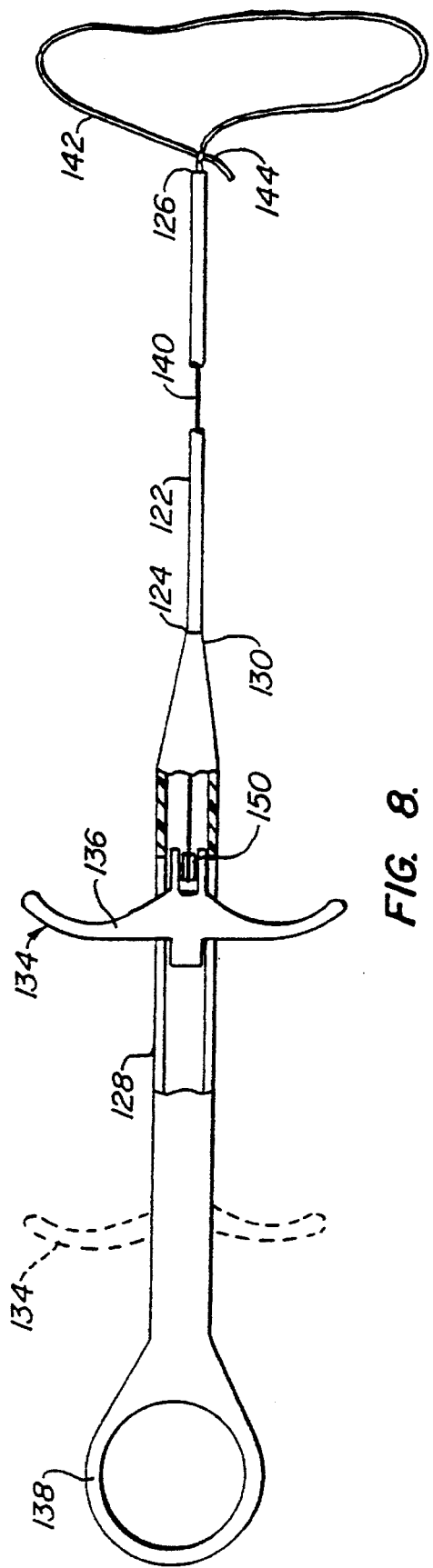
FIG. 8 is a top plan view with portions broken away of the embodiment of the suture applying device of FIG. 7.

Referring now to FIGS. 7 and 8, a further preferred embodiment 120 of the suture applying device of the present invention will be described. The device 120 includes a shaft 122 having a proximal end 124 and a distal end 126. An elongate handle 128 is secured at its distal end 130 to the proximal end 124 of the shaft 122. Handle 128 includes a hollow interior and defines an elongate slot 132. A puller 134 includes a pair of finger-retaining ears 136 slidably mounted in the slot 132 so that it may be shifted between a distal position (shown in full line in FIG. 8) and proximal position (shown in broken line). The handle 128 will typically terminate in a thumb retainer, such as the thumb ring 138 at its proximal end. In this way, the treating physician may hold the device 120 with the thumb within thumb-retaining ring 138 and middle and index fingers on the finger retaining ears 136, in a conventional manner.

A length of suture 140 includes an open loop 142 and a free end extending proximally from the open loop. The open loop 142 is held outside the distal tip 126 of shaft 122 with a slip-knot 144 being located adjacent an open distal port of the lumen in the shaft, the slip-knot being larger than the distal port to prevent passage therethrough. The free end of the suture 140 passes through the open port and proximally through the lumen of shaft 122. After passing through the lumen, the free end of the suture 140 enters the interior of housing 128, where it is received over a pulley 150 mounted on puller 134. The free end of suture 140 is secured to an anchor point 151 fixed to the interior of housing 128. In this way, proximal retraction of the puller 34 draws the free end of suture 140 proximally at a rate twice that of the rate which the puller is drawn. It will be appreciated that an even greater increase in the rate of suture translation could be achieved by placing a second pulley (not illustrated) on the housing and passing the free end of the suture over the second pulley and attaching it to the puller. In this way, a 3:1 ratio of uptake to pulley withdrawal could be achieved.

Referring now to FIG. 9A, a suture applying system 150 includes a suture applying device 152 which may take the form of any of the previously described embodiments. The suture applying device will include a housing 154, an actuator 156, and a shaft 158. The system 150 further comprises a sheath 160 slidably disposed over a distal portion of the shaft 158. A suture to be applied by the device has, as described above, a free end carried within shaft 158 coupled to actuator 156 at its proximal end and extending through a distal port in shaft 158 to a loop 162 residing outside of the shaft. Loop 162 may be disposed distal to the distal end of shaft 158, or adjacent a lateral surface of shaft 158, surrounded by sheath 160. Loop 162 is thereby protected within the sheath, but may be exposed by sliding the sheath 160 in a proximal direction over the shaft 158.

The sheath 160 is intended to be introduced through a trocar sleeve or other cannula 164 which is sized to receive the sheath within a central lumen 166 thereof. The cannula 164 may comprise a restriction 168, illustrated as a narrowing of central lumen 166 in the proximal end of the cannula. Restriction 168 is sized to mate with a protrusion 170, illustrated as a flare at the proximal end of sheath 160. Protrusion 170 may alternatively comprise a bump, retaining ring, rim, or similar structure. In this way, the sheath 160 may be freely introduced through the trocar 164 until the protrusion 170 engages the restriction 168. Alternatively, the cannula may be of substantially constant interior diameter without a restriction, in which case the protrusion would engage the proximal end surface of the cannula. At that point, further distal travel of the sheath is prevented, and the sheath will be automatically retracted relative to the distal end of shaft 158 as the suture applier is further pushed through the cannula. Thus, loop 162 will be introduced out the distal end 172 of the cannula 164, where it will be available for use at a desired target location.

The suture applying system of the present invention is particularly advantageous due to the reduced trauma the system inflicts upon the patient. This is accomplished by providing a self-introducing cannula 168 having a diameter smaller than conventional trocar sleeves which eliminates the need for positioning an additional trocar sleeve to introduce the suture applier. As shown in FIG. 9B, the self-introducing cannula 168 includes a stylet 180 having a sharpened distal tip 182 for penetrating tissue, a rigid shaft 184, and a knob 186 on the proximal end of the shaft suitable for grasping with the fingers and pushing with the thumb. Stylet 180 may be slidably positioned in central lumen 166 of cannula 164 with distal tip 182 of the stylet extending beyond distal end 172 of the cannula. In this way, the cannula 164 may be positioned in the body of the patient by exerting a distal force on knob 186 such that tip 182 penetrates body tissue. Taper 188 on cannula 164 facilitates introduction of the cannula through the penetration created by stylet tip 182. Once the cannula has been positioned as desired, stylet 180 may be removed from central lumen 166, to allow introduction of the suture applier.

In a preferred embodiment, the cannula 164 and stylet 180 will be of significantly small cross-section than conventional trocars. Central lumen 166 of the cannula will have a diameter large enough to facilitate introduction of stylet 180 and shaft 158 of the suture applier, which will be as small as 12–14 gauge or smaller for a suture size 0. For small suture sizes, such as size 2-0, shaft 158 and stylet 180 may be of even smaller diameter. As a result, the outer diameter D of cannula 164 may be as small as 2.5 mm or less, as compared to conventional trocars which have an outer diameter typically in the range of 5 mm to 6 mm. The small diameter of the self-introducing cannula of the suture applying system of the present invention therefore results in significantly less trauma than devices which require the use of conventional trocars.

Figure 10F:
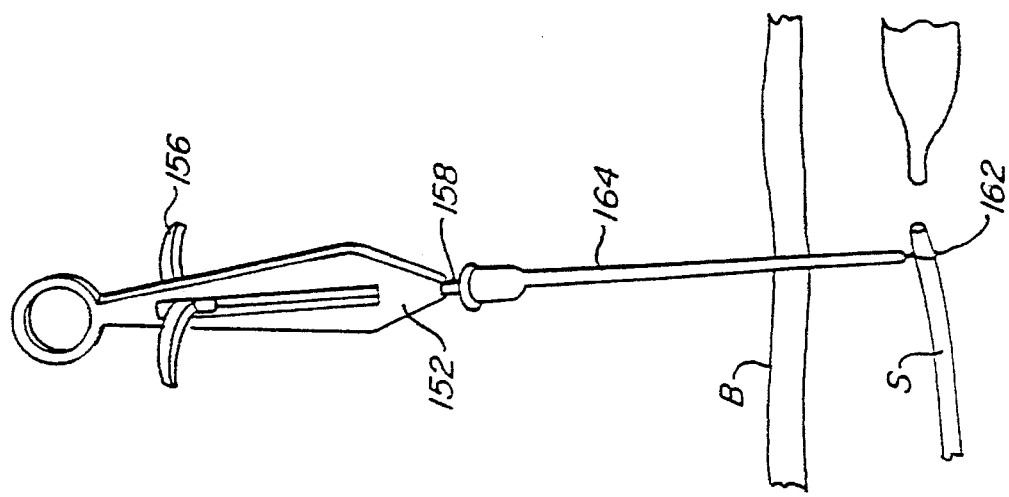
Figure 10E:
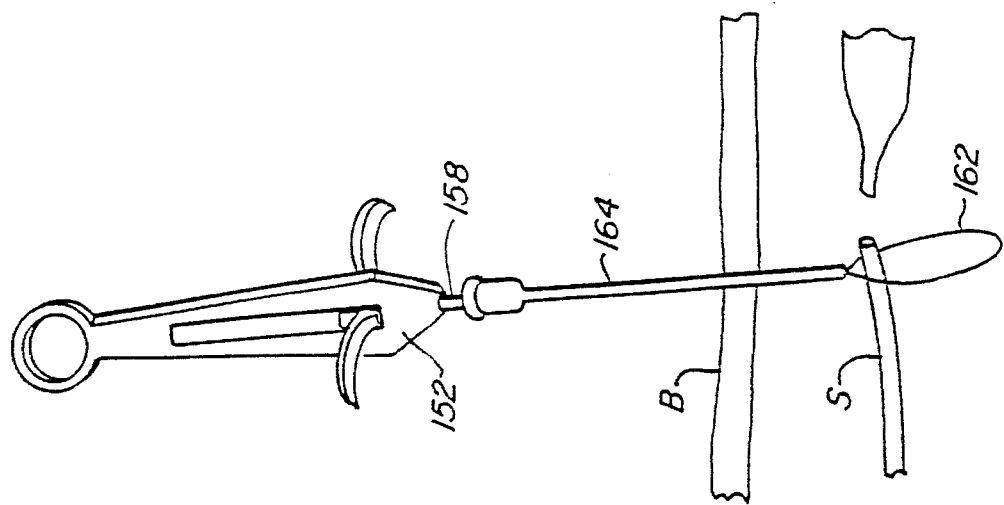
Figure 10D:
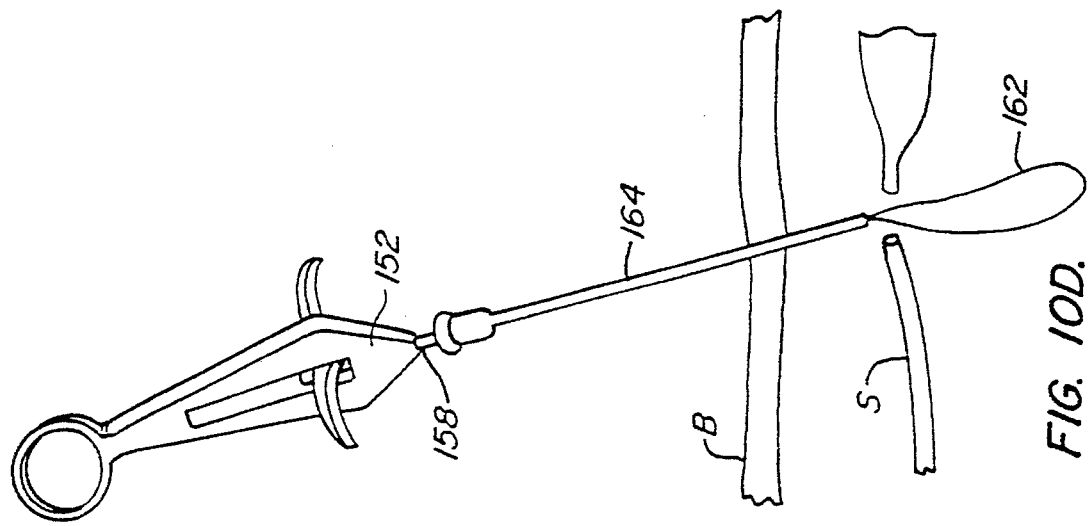

Use of the suture applying system 150 of the invention is illustrated in FIGS. 10A–10F. A body structure S to be sutured is located within a body cavity such as the abdomen, beneath a body surface B, which may be, for example, the abdominal wall (FIG. 10A). Cannula 164 may be self-introduced using an internal stylet 180 having a sharpened tip 182 which extends from the distal end of the cannula. In this way, the distal end of the cannula may be positioned adjacent the body structure S, as illustrated in FIG. 10B. The stylet is then withdrawn and the suture applier introduced through the proximal end of the cannula 164 with sheath 160 surrounding a distal portion of shaft 158, as illustrated in FIG. 10C. The suture applier is fully introduced until protrusion 170 of sheath 160 engages restriction 168, causing the distal end of shaft 158 carrying suture loop 162 to emerge from the distal end of cannula 164, as illustrated in FIG. 10D. The suture loop 162 may then be positioned over the body structure S, as illustrated in FIG. 10E, and the suture loop 162 tightened by drawing proximally on puller 156, as illustrated in FIG. 10F. The tightened suture loop may then be cut, typically using separately introduced cutters, and the suture applier and cannula 164 removed from the body cavity.

Figure 11:
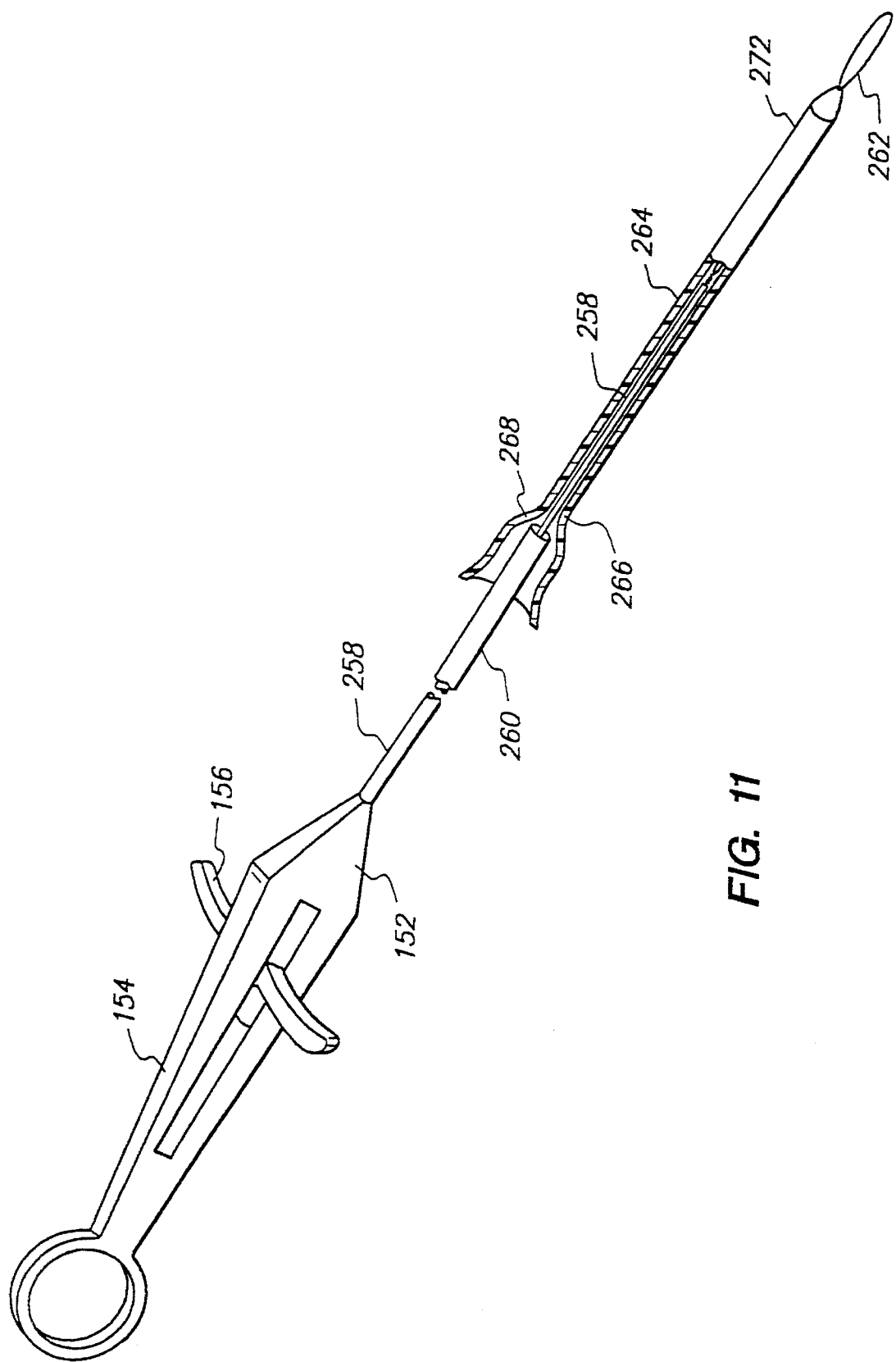
FIGS. 11–13 are a cross sectional views of alternative suture applying systems constructed in accordance with the principles of the present invention.
Figure 12:
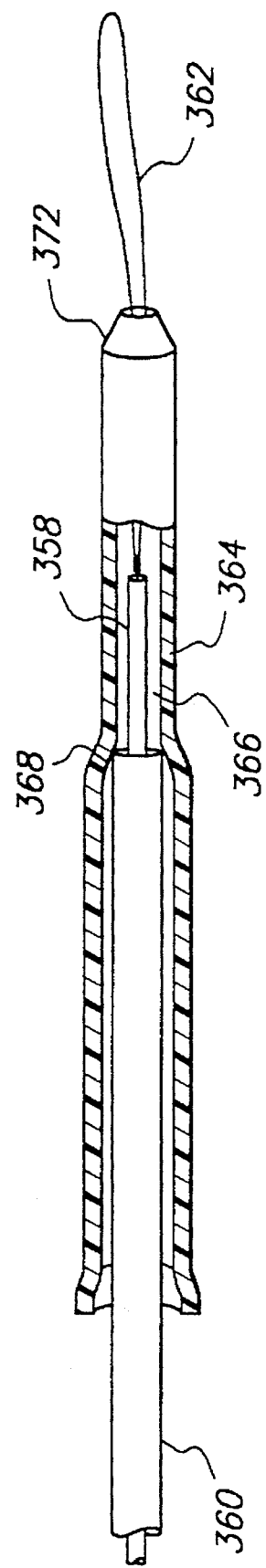
Figure 13:
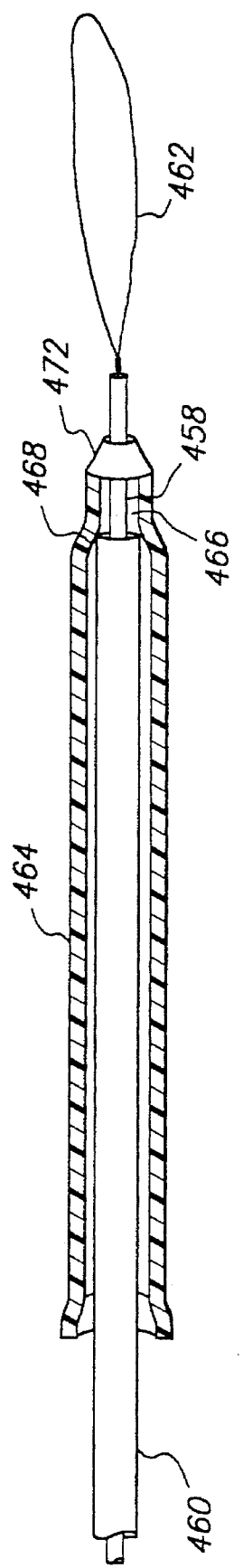

Alternative embodiments of the suture applying system 150 are shown in FIGS. 11–13. These embodiments include a sheath protecting the suture loop similar to FIG. 9. Unlike the system in FIG. 9, however, these embodiments prevent the sheath from intruding into the body cavity. This is accomplished by a restriction at any point along the cannula which retracts the sheath to expose the loop. Thus, the loop is protected by the sheath while in the cannula until the restriction is reached. At this point, the sheath is retracted exposing the loop during the loop's remaining travel through the cannula. Such a configuration is particularly useful when space in the abdominal cavity is limited, as is the case with thin patients and/or with use in the lower abdominal cavity, since the sheath is not allowed to extend through the cannula. Further, because the sheath is retracted prior to passing through the distal end of the introducer cannula, longer sheath lengths, and thus larger loop sizes, can be used even while working with limited abdominal cavity space.

The embodiment shown in FIG. 11 is configured so that sheath 260 engages the proximal end of the cannula 264 enabling the suture to advance through the central lumen 266 of the cannula 264 without the sheath 260. Preferably, engagement will be accomplished by sizing the outer diameter of the sheath 260 to be larger than the inner diameter of the central lumen 266 of the cannula 264. The outer diameter of the shaft 258 (shown in broken line) has a diameter less than the diameter of the central lumen 266 of the cannula 264 so that is can pass through the cannula. With this configuration, the sheath 260 may be introduced into the cannula 264 until the distal end of the sheath 260 contacts the restriction 268 in the cannula 264 (which is equal to the inner diameter of the central lumen 266). Thus, the shaft 258 passes through the lumen 266 while the sheath 260 will be automatically retracted over the shaft 258 as the shaft 258 is further advanced through the cannula 264. Thus, loop 262 will be able to pass out the distal end 272 of the cannula 264 and into the patient's body cavity. Alternatively, the sheath 260 could have a protrusion (not shown) at its distal end to engage the proximal end of the cannula 264.

In FIG. 12, a distal end of sheath 360 engages cannula 364 at a midpoint between its proximal and distal ends. Preferably, this will be accomplished by forming a restriction or narrowing 368 in the middle of the central lumen 366 so that the distal end of the sheath 360 will engage the cannula 364 at the restriction 368 thereby retracting the sheath 360 and exposing the suture. The suture may then be extended through the distal end of the cannula 364 as previously discussed.

The embodiment in FIG. 13 is similar to the embodiment in FIG. 12 except that the restriction or narrowing 468 is located at or near the distal end of the cannula 464. With this configuration, the sheath 460 covers the suture until the sheath 460 engages restriction 468 thereby uncovering the suture and allowing it to extend through the cannula 464 as previously discussed.

The embodiments discussed in connection with FIGS. 11–13 allow the sheath to be longer than the sheath in FIG. 9 because the sheath does not extend into the body cavity. As sheath lengths are increased with these embodiments, however, the distance that the shaft may be introduced into the body cavity is reduced because of earlier contact with the sheath and the handle of the suture applier. Thus, a collapsible sheath structure as shown in FIGS. 14–16 can be used to allow further travel of the shaft into the body cavity while allowing longer sheaths and larger loop sizes.

Figure 14:
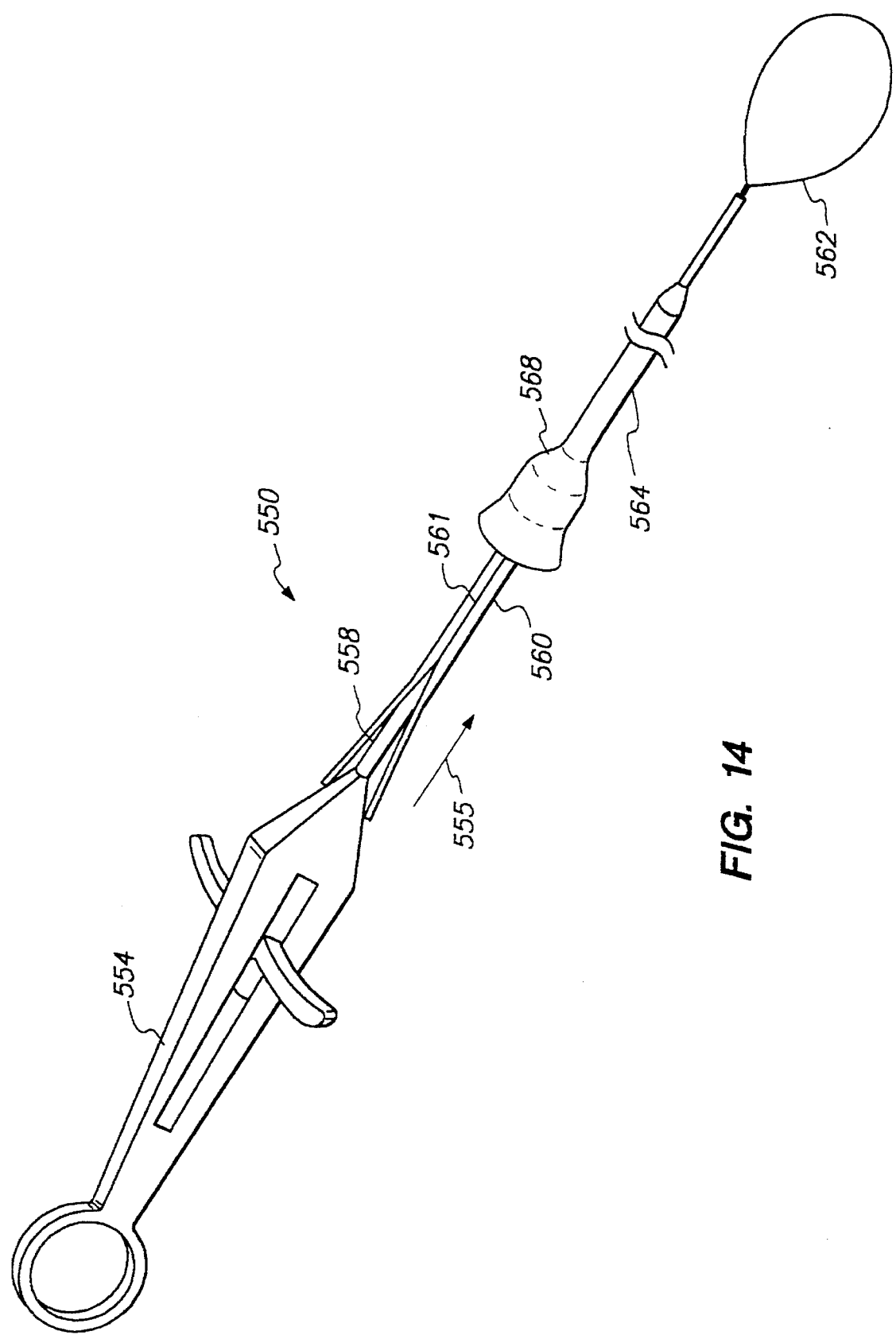
FIG. 14 is a perspective view of a suture applying system showing the sheath being separated along an axial line as the handle is advanced through the sheath.

In FIG. 14, the suture applying system 550 has a sheath 560 that will split axially as the handle 554 is axially advanced in the distal direction (arrow 555). To facilitate splitting, the sheath 560 can have a score 561 along an axial line. As the sheath 560 is split, it will peel off the shaft 558 allowing further passage of the shaft 558 into the abdominal cavity. With this configuration, longer sheath lengths which accommodate larger loop sizes, can be used while maintaining an adequate proximity between the handle of the suture applier and the target anatomy.

Figure 15:
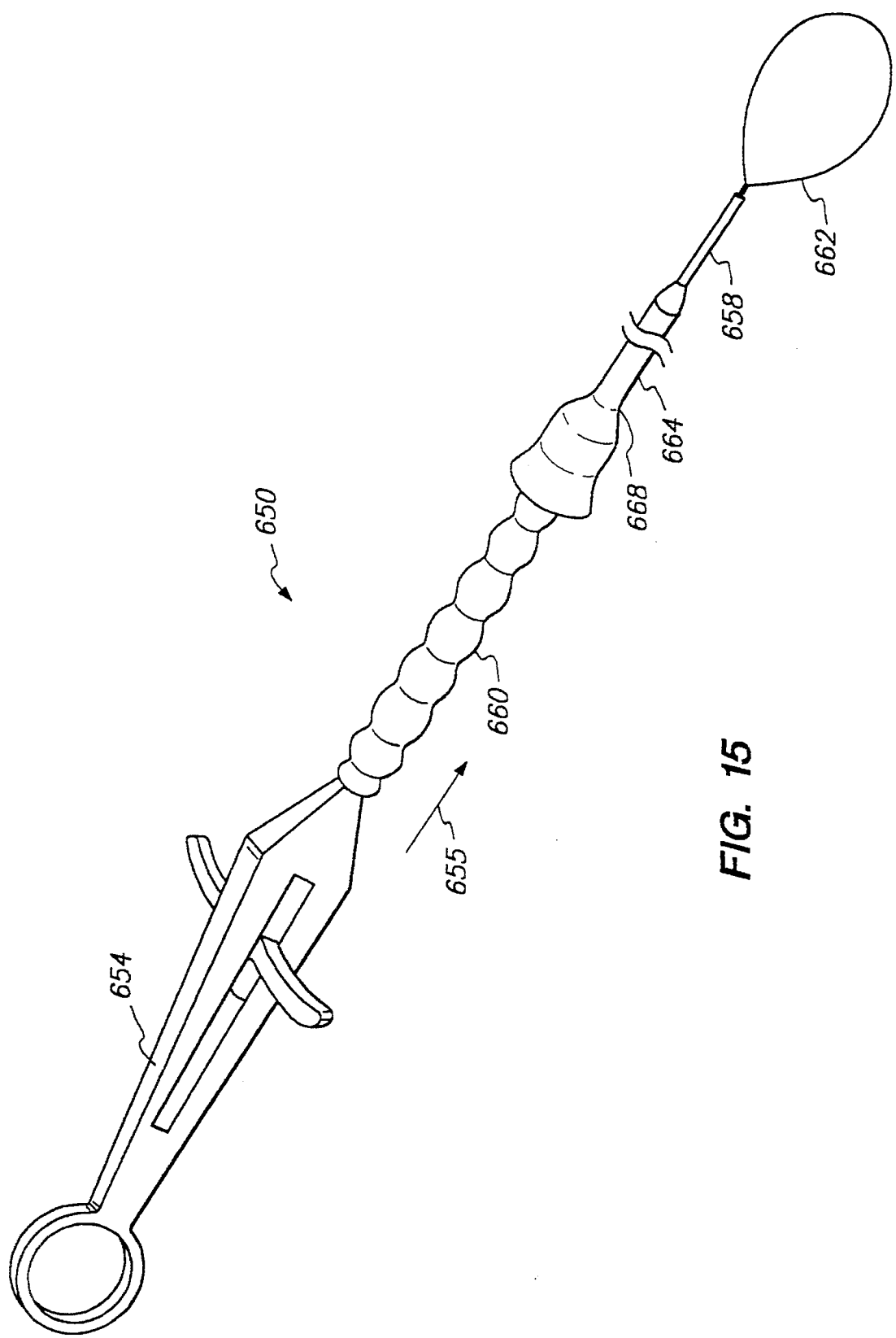
FIG. 15 is a perspective view of a suture applying system showing a sheath constructed with a compressible tube.
Figure 16:
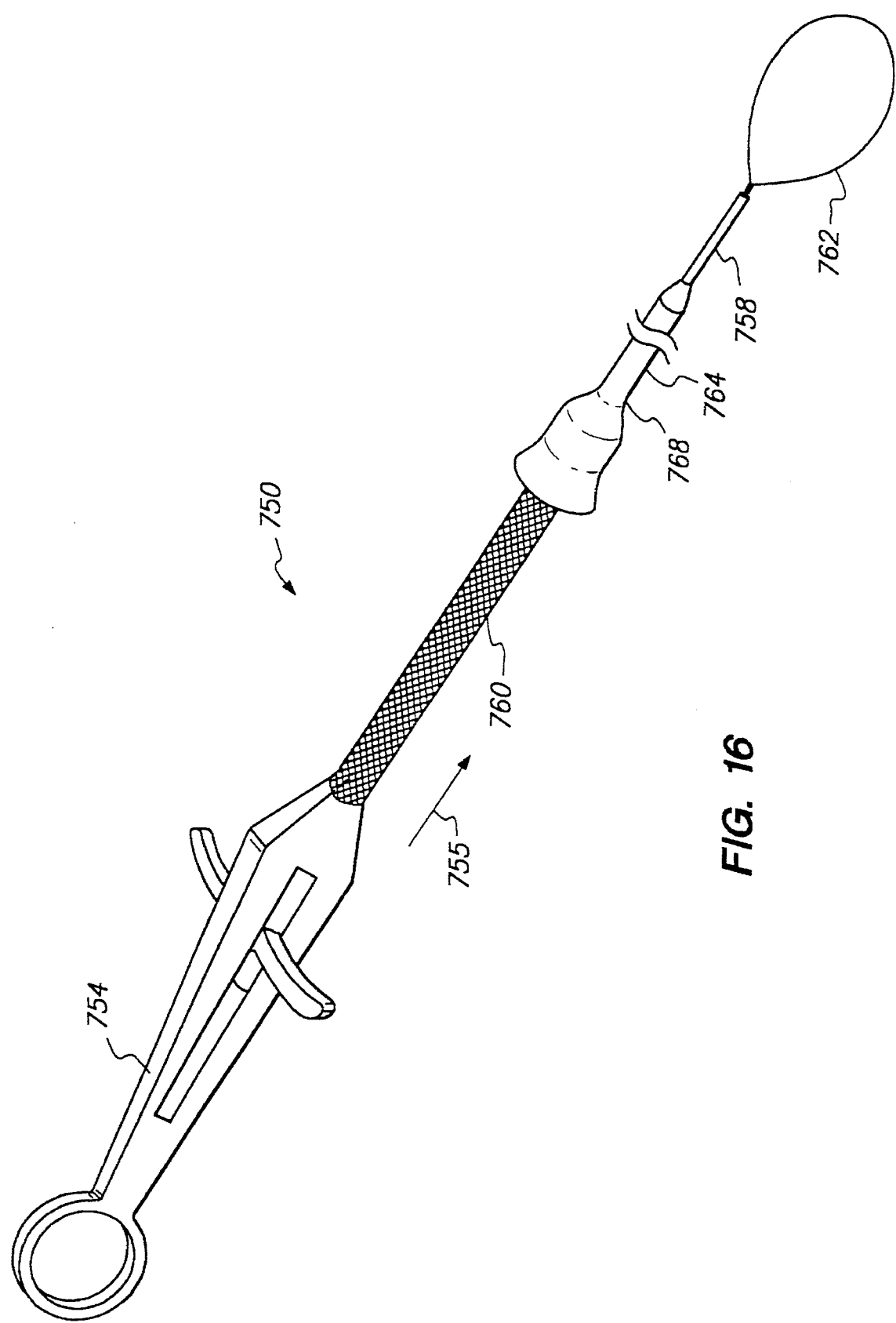
FIG. 16 is a perspective view of a suture applying system showing a sheath constructed with a braided or woven mesh material.

Alternatively, as shown in FIGS. 15 and 16, the sheath can be constructed of a compressible tube or the like so that the tube axially collapses as a force is applied to the suture applier. As shown in FIG. 15, sheath 660 can have a convoluted wall which permits the shaft to fold or "accordion" as the handle 654 is advanced. As shown in FIG. 16, the sheath 760 can be constructed of a braided or woven mesh material or the like that collapses under a load.

Although the foregoing invention has been described in some detail by way of illustration and example, for purposes of clarity of understanding, it will be obvious that certain changes and modifications may be practiced within the scope of the appended claims.

What is claimed:

1. A system for applying a suture loop through a cannula having a central lumen, said system comprising:

a suture loop applier including a handle connected to a shaft, a length of suture loop having a free end and a loop at another end, wherein the loop extends from a distal end of the shaft; and a sheath slidably mounted on the shaft to move between an extended position wherein the suture loop is covered and a retracted position wherein the suture loop is uncovered.

2. A system as in claim 1, wherein a distal end of the sheath is configured to engage with a proximal end of the cannula, whereby engagement of the distal end of the sheath with the proximal end of the cannula will cause the sheath to slide proximally on the shaft allowing the suture to advance entirely through the lumen uncovered by the sheath.

3. A system as in claim 2, wherein the sheath has an outer diameter that is greater than an inner diameter of the central lumen of the cannula, so that the distal end of the sheath is engagable with the proximal end of the cannula.

4. A system as in claim 1, further comprising a protrusion at a proximal end of the sheath for engagement with a proximal end of the cannula, whereby the suture is advanced cable through the lumen while covered by the sheath until the protrusion engages the cannula to retract the sheath.

5. A system as in claim 4, further comprising a restriction at the proximal end of the cannula for engagement with the protrusion of the sheath.

6. A system as in claim 1, wherein a distal end of the sheath is configured to engage with a distal end of the cannula, whereby the suture is allowed to advance through the lumen covered by the sheath until engagement of the distal end of the sheath with the distal end of the cannula.

7. A system as in claim 6, further comprising a restriction at the distal end of the cannula for engagement with the sheath.

8. A system as in claim 1, wherein a distal end of the sheath is configured to engage the cannula at a midpoint between a proximal and a distal end thereof, whereby the suture is covered by the sheath during a portion of the sheath's advancement through the cannula lumen.

9. A system as in claim 8, further comprising a restriction at the midpoint of the cannula for engagement with the sheath.

10. A system as in claim 1, wherein the sheath is scored along an axial line to facilitate splitting as the handle is advanced therethrough.

11. A system as in claim 1, wherein the sheath is axially compressible.

12. A system as in claim 11, wherein the sheath is constructed of a braided or woven mesh material, whereby the sheath will compress upon contact with the handle.

13. A system as in claim 11, wherein the sheath is a tube having a convoluted wall.

14. A system for applying a suture loop through a cannula having a central lumen, said system comprising:

a suture loop applier including a handle connected to a shaft, a length of suture loop having a free end and a loop at another end, wherein the loop is held at a distal end of the shaft;

a sheath slidably mounted on the distal end of the shaft, said sheath covering the suture loop, said sheath having an outer diameter greater than an inner diameter of the central lumen of the cannula whereby the sheath is prevented from entering the proximal end of the central lumen of the cannula;

said shaft having an outer diameter less than the inner diameter of the cannula such that the shaft may be extended through the cannula while the sheath is prevented from entering the central lumen of the cannula, thereby causing the sheath to slide proximally on the shaft to expose the suture loop through a distal end of the cannula.

15. A method for applying a suture loop into a body cavity, said method comprising:

introducing a cannula having a central lumen into the body cavity;

introducing a suture loop protected by a sheath into the cannula;

engaging the cannula with the sheath so that the sheath is held stationary relative to the cannula; and advancing the suture loop through the lumen and into the body cavity.

16. A method as in claim 15, wherein the step of introducing the cannula includes introducing the cannula with an internal stylet, the method further comprising removing the stylet prior to introducing the suture loop and the sheath into the cannula.

17. A method as in claim 15, further comprising a step of placing the loop around a body structure in the body cavity and tightening the loop around the structure after the advancing step.

18. A method as in claim 15, wherein the engaging step includes engaging a proximal end of the cannula with a distal end of the sheath, and the advancing step includes advancing the suture entirely through the lumen without the sheath.

19. A method as in claim 15, wherein the engaging step includes engaging a distal end of the cannula with a distal end of the sheath so that the suture is covered by the sheath as it advances through the lumen.

20. A method as in claim 15, wherein the engaging step includes engaging a proximal end of the cannula with a proximal end of the sheath, and the advancing step includes advancing the suture through the lumen covered by the sheath until a protrusion engages the cannula to retract the sheath.

21. A method as in claim 15, wherein the engaging step includes engaging the cannula at a midpoint between the proximal and distal ends thereof with a distal end of the sheath, so that the suture is covered by the sheath during at least part of the advancing step.

22. A method for applying a suture loop into a body cavity, said method comprising:

introducing a cannula into a patient;

providing a suture applier including a shaft, a length of suture having a free end and a pre-formed loop, a handle connected to a proximal end of said shaft, and a sheath on the distal end of the shaft protecting the preformed loop;

introducing the suture applier and the sheath into the cannula: and exposing the suture loop through the distal end of the cannula.

23. A method as in claim 22, wherein the step of introducing the cannula includes introducing the cannula with an internal stylet, the method further comprising a step of removing the stylet prior to introducing the suture applier and the sheath into the cannula.

24. A method as in claim 22, further comprising the steps of engaging a proximal end of the cannula with a distal end of the sheath and advancing the suture entirely through the lumen without the sheath.

25. A method as in claim 22, further comprising the steps of engaging a distal end of the cannula with a distal end of the sheath and advancing the suture so that the suture is covered by the sheath as it advances through the lumen.

26. A method as in claim 22, further comprising the steps of engaging a proximal end of the cannula with a proximal end of the sheath and advancing the suture through the lumen covered by the sheath until a protrusion engages the cannula to retract the sheath.

27. A method as in claim 22, further comprising the steps of engaging the cannula at a midpoint between the proximal and distal ends thereof with it distal end of the sheath and advancing the suture so that the suture is covered by the sheath during a portion of the sheath's advancement through the cannula lumen.

28. A method as in claim 22, further comprising a step of separating the sheath along an axial score as the handle contacts the sheath and is advanced therethrough.

29. A method as in claim 22, further comprising a step of axially compressing the sheath as the handle contacts the sheath and is further advanced.

30. A method for applying a suture loop into a body cavity, said method comprising:

introducing a cannula having a central lumen into a patient;

providing a suture applier including a shaft, a length of suture having a free end and a pre-formed loop, a handle connected to a proximal end of said shaft, and a sheath on the distal end of the shaft protecting the preformed loop, the sheath having an outer diameter greater than an inner diameter of the central lumen of the cannula, the shaft having an outer diameter less than the inner diameter of the central lumen of the cannula;

introducing the suture applier and the sheath into the cannula thereby retracting the sheath along the shaft and exposing the suture loop through the distal end of the cannula.

31. Apparatus for applying and tightening a suture loop, said apparatus comprising:

a hollow shaft having a proximal end and a distal end;

a length of suture having a free end and a loop at another end, wherein the loop is held at the distal end of the shaft and the free end of the suture extends through the hollow shaft to the proximal end;

a handle assembly comprising a housing having a protected interior attached to the proximal end of the shaft, said handle assembly including a slidably mounted actuator, said actuator comprising a puller; and a pulley on the puller positioned entirely within the protected interior, wherein the free end of the suture travels around the pulley and is secured to the handle, said pulley coupling the puller to the free end of the suture so that the free end is drawn proximally by the puller at a faster rate than the puller, whereby drawing proximally on the puller will tighten the suture loop.

32. Apparatus for applying and tightening a suture loop, said apparatus comprising:

a hollow shaft having a proximal end and a distal end;

a length of suture having a free end and a loop at another end, wherein the loop is held at the distal end of the shaft and the free end of the suture extends through the hollow shaft to the proximal end;

a handle assembly comprising a housing having a protected interior attached to the proximal end of the shaft, said handle assembly including a slidably mounted actuator, said actuator comprising a pusher; and a pulley rotatably mounted in the interior of the housing having a small gear wheel and a large uptake wheel attached to the free end of the suture, wherein the pusher includes a gear face which mates with the gear wheel, said pulley coupling the pusher to the free end of the suture so that the free end is drawn proximally by the pusher at a faster rate than the pusher, whereby drawing proximally on the pusher will tighten the suture loop.

33. Apparatus for applying and tightening a pre-tied suture loop, said apparatus comprising:

a shaft having proximal and distal ends;

a length of suture having a free end and a knotted loop at the other end, wherein said knotted loop is held on the distal end of the shaft; and a handle assembly attached to the proximal end of the shaft and having means for selectively engaging and proximally translating the free end of the suture, whereby the free end may be successively engaged and drawn proximally to close the knotted loop.

34. Apparatus as in claim 33, wherein the shaft is a tube having a lumen which receives the free end of the suture, wherein the loop is held on an open distal port of the lumen.

35. Apparatus as in claim 33, wherein the loop has a diameter which is larger than a size which can be drawn closed around an object in a single stroke of the engaging means.

36. Apparatus as in claim 33, wherein the means for selectively engaging and translating the free end of the suture comprises a pair of opposed jaws, wherein each jaw has an attached finger retainer and the handle includes a thumb retainer, whereby the apparatus can be manipulated using the thumb and two fingers of a single hand.

37. Apparatus as in claim 36, wherein the opposed jaws are spring-biased away from each other.

38. Apparatus as in claim 37, wherein the opposed jaws define opposed gripping surfaces which firmly grip the suture when the jaws are closed together.

* * * * *